(12) United States Patent
Steele, Sr. et al.

(10) Patent No.: US 6,572,527 B2
(45) Date of Patent: Jun. 3, 2003

(54) RADIOACTIVE SEED-HOLDING DEVICE

(75) Inventors: Martin T. Steele, Sr., Otsego, MN (US); Scott Henderson, Palm Harbor, FL (US); Joseph Harms, Clearwater, FL (US)

(73) Assignee: Mentor Corporation, Santa Barbara, CA (US)

( * ) Notice: Subject to any disclaimer, the term of this patent is extended or adjusted under 35 U.S.C. 154(b) by 0 days.

(21) Appl. No.: 09/792,307

(22) Filed: Feb. 23, 2001

(65) Prior Publication Data

US 2002/0120174 A1 Aug. 29, 2002

(51) Int. Cl.[7] .......................... A61N 5/00; A61M 31/00
(52) U.S. Cl. .......................................... 600/7; 604/57
(58) Field of Search .................. 600/1, 3, 6, 7, 600/427, 437, 5, 8, 9–595; 376/158; 606/130; 604/57, 59–62, 64

(56) References Cited

U.S. PATENT DOCUMENTS

| | | | |
|---|---|---|---|
| 4,402,308 A | | 9/1983 | Scott |
| 4,461,280 A | | 7/1984 | Baumgartner |
| 4,700,692 A | | 10/1987 | Baumgartner |
| 4,969,863 A | | 11/1990 | van't Hooft et al. |
| 5,242,373 A | | 9/1993 | Scott et al. |
| 5,342,283 A | * | 8/1994 | Good .......................... 376/158 |
| 5,562,594 A | * | 10/1996 | Weeks ............................ 600/3 |
| 5,860,909 A | | 1/1999 | Mick et al. |
| 5,957,935 A | * | 9/1999 | Brown et al. ................ 600/437 |
| 6,102,844 A | * | 8/2000 | Ravins et al. ................... 600/7 |
| 6,256,529 B1 | * | 7/2001 | Holupka et al. ............. 600/427 |
| 6,267,717 B1 | * | 7/2001 | Stoll et al. ...................... 600/1 |
| 6,270,472 B1 | * | 8/2001 | Antaki et al. ................... 600/7 |
| 6,350,227 B1 | * | 2/2002 | Shikhman et al. .............. 600/7 |
| 6,358,195 B1 | * | 3/2002 | Green et al. .................... 600/7 |
| 6,361,487 B1 | * | 3/2002 | Green et al. .................... 600/6 |
| 6,366,633 B1 | | 4/2002 | Stezaly et al. |
| 6,409,651 B1 | * | 6/2002 | Brown, III ...................... 600/3 |
| 2002/0013509 A1 | | 1/2002 | Schmidt |

OTHER PUBLICATIONS

"Transperineal Ultrasound–Guided Prostate Seed Implant Accessories," The Complete Accessories Guide for the Seattle or Mick® Prostate Seed Delivery Systems! Mick Radio–Nuclear Instruments, Inc., 4 pgs.
"Product Update 98," Product Brochure, Mick Radio–Nuclear Instruments, Inc., 8 pgs.
"Mick® 200–TPV Applicator," Product Brochure, Mick Radio–Nuclear Instruments, Inc., 4 pgs.
"Mick® 200–TP Applicator Kit," Product Brochure, Mick Radio–Nuclear Instruments, Inc., 6 pgs.
"Prostate Brachytherapy," Mick News Flash 2000, 2000, vol. 1, Issue 1, Mick Radio–Nuclear Instruments, Inc., 6 pgs.
"Brachytherapy Seed Magazine Disposable, Spring-Loaded," Product Specification, Mick Radio–Nuclear Instruments, Inc., 2 pgs.
"Transperineal Ultrasound–Guided Prostate Seed Implants—The "Mick" System," Instrumentation and Accessories Guide, Mick Radio–Nuclear Instruments, Inc., 4 pgs.
"Transperineal Ultrasound–Guided Prostate Seed Implant Accessories," The Complete Accessories Guide for the Seattle or Mick® Prostate Seed Delivery Systems! Mick Radio–Nuclear Instruments, Inc., 18 pgs.

* cited by examiner

Primary Examiner—Eric F. Winakur
Assistant Examiner—Nikita R Veniaminov
(74) Attorney, Agent, or Firm—Fish & Richardson, P.C., P.A.

(57) ABSTRACT

An apparatus is described that efficiently resupplies radioactive seeds to a brachytherapy applicator. A seed-holding system includes a holder and a transfer device. The holder, which may be disposable, stores the radioactive seeds and the transfer device, which may be reusable, helps shield and dispense the seeds. The holder is coupled to the transfer device, and the apparatus is mated to an applicator. After seeds have been dispensed, the apparatus may be disconnected from the applicator and the empty holder may be ejected from the transfer device, and replaced with a full holder.

49 Claims, 8 Drawing Sheets

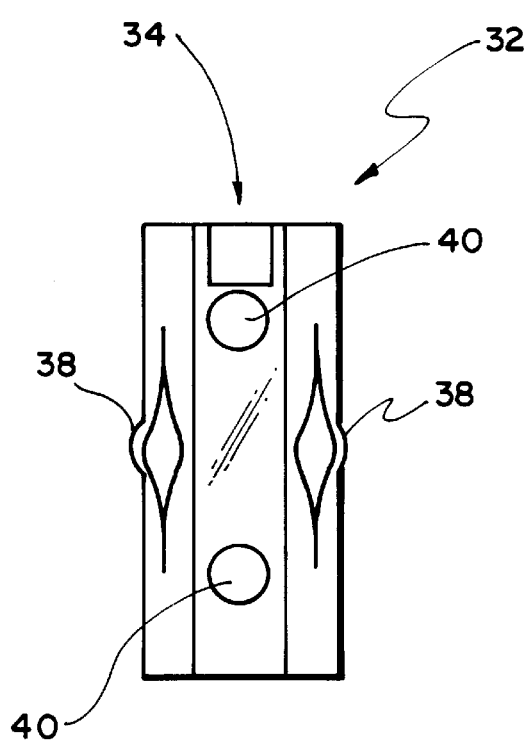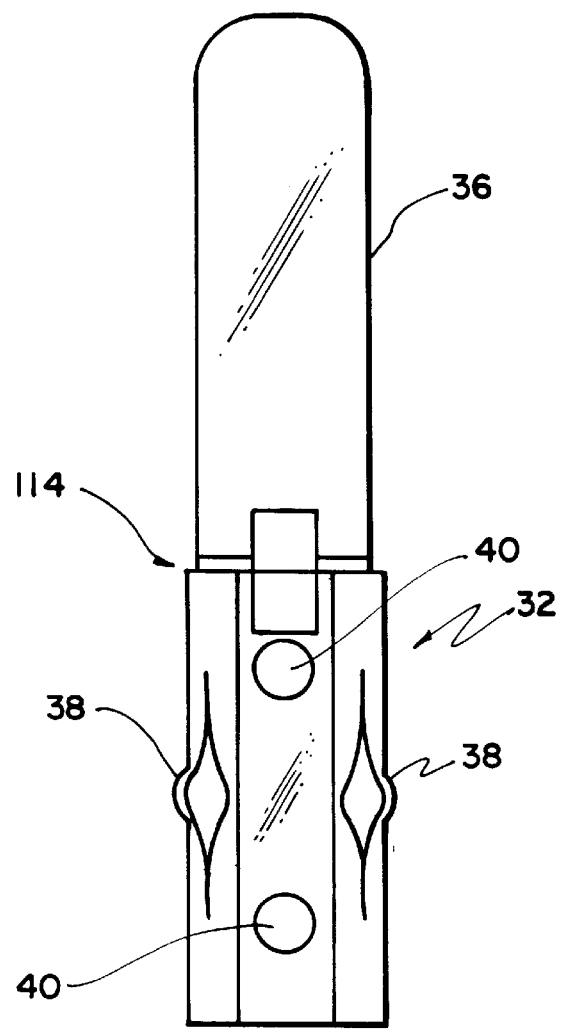
FIG. 6A
FIG. 6B

RADIOACTIVE SEED-HOLDING DEVICE

BACKGROUND

This invention relates to medical devices and, more particularly, to medical devices useful in providing brachytherapy.

Brachytherapy is a form of cancer treatment, in which radiation sources placed inside the patient's body irradiate a tumor. In brachytherapy, a surgeon usually implants several radioactive seeds in or around the tumor, thus providing a higher radiation dose to the tumor than would be possible with external beam radiation therapy. Careful placement of the radioactive seeds allows localized and precise irradiation of the tumor. Because the radiation dose diminishes rapidly outside the radioactive seed, the radiation dose to surrounding healthy tissues is reduced.

Radioactive seeds typically are tiny (usually 1 mm by 4.5 mm), roughly cylindrical objects containing very small amounts of radioactive material. In one widely practiced brachytherapy procedure, the radioactive seeds are implanted permanently inside the patient's body. The half-life of the radioactive material is generally short, and the radioactivity in the seeds decays after about three to six months to the point that there is little detectable radiation. Two radioactive isotopes commonly used for permanent implants are iodine-125, often used to treat slower growing tumors, and palladium-103, which is preferred when the tumor is fast-growing. Other radioactive materials have been used in implants as well.

Many forms of cancer respond to brachytherapy, including several forms of prostate cancer. Brachytherapy is generally less invasive than surgery, usually results in fewer side effects for the patient than surgery or external beam radiation, allows for a short recovery time and reduces the impact upon the patient's quality of life.

SUMMARY

In brachytherapy treatment, it is common for the physician to implant a large number of seeds in the patient's tissue. In a typical prostate implantation, for example, eighty to one hundred twenty radioactive seeds may be implanted at varying positions in and around the prostate. The physician uses a device called an applicator to perform the implantation. The applicator usually includes a slender push rod (or stylet) to push the radioactive seeds into a hollow implantation needle. The implantation needle, which is usually coupled to the applicator, penetrates the patient's body and is used to deliver the seeds to the tumor and the area around the tumor. Typically, the surgeon advances a radioactive seed through the needle to a desired location. To deliver multiple seeds, the surgeon can repeatedly place seeds into the void space created by retracting the needle. In some brachytherapy procedures, several implantation needles may be employed, each needle penetrating the patient at a different site. In such a procedure, a single applicator may be used for all of the implantations, the applicator coupled to each needle in turn. In other brachytherapy procedures, a single applicator and a single needle may be used for implantations at several sites.

Usually the applicator contains a supply of radioactive seeds for implantation. Typically the radioactive seeds are supplied in the form of a cartridge or magazine, which is mated to the applicator. The number of seeds supplied by the cartridge or magazine is usually less than the total number of seeds needed for the brachytherapy procedure. Accordingly, the applicator may need to be resupplied with seeds several times during the procedure. The seed-holding system and techniques described below facilitate the rapid resupply of seeds to an applicator. The seed-holding system provides for a holder, which may be disposable, and a transfer device, which may be reusable. The holder stores the radioactive seeds. Several holders loaded with radioactive seeds may be prepared for a single brachytherapy procedure. The transfer device helps dispense the seeds from the holder, and also provides shielding to the seeds, reducing the risk to medical staff of radiation exposure. When the holder is coupled to the transfer device, the seed-holding system can be mated to an applicator, and radioactive seeds may be dispensed from the holder. When the holder is emptied of seeds, the seed-holding system may be disconnected from the applicator, and the empty holder may be ejected from the transfer device. A fresh, full holder may then be coupled to the transfer device, and the seed-holding system may once again be mated to the applicator. The implantation of seeds may then continue. The resupply of seeds may be completed in a matter of seconds.

In one embodiment, the present invention provides a device, including a holder and a transfer device. The holder, which is configured to receive one or more radioactive seeds, includes two components: a main body and a pusher. Both parts may be made of plastic. The holder is further configured to mate to an applicator, and to dispense seeds from the holder's distal end. The transfer device, which is configured to engage the holder, is composed of several components, including a housing, an expansive spring and a pusher assembly. The transfer device may further include a shield that can be extended to provide radiation shielding around the holder.

Other advantages, features and embodiments of the invention will become apparent from the following detailed description and from the claims.

DESCRIPTION OF DRAWINGS

FIG. 6A is a front view of a pusher.

FIG. 6B is a front view of the pusher shown in FIG. 6A, with a handle.

DETAILED DESCRIPTION

Figure 1:
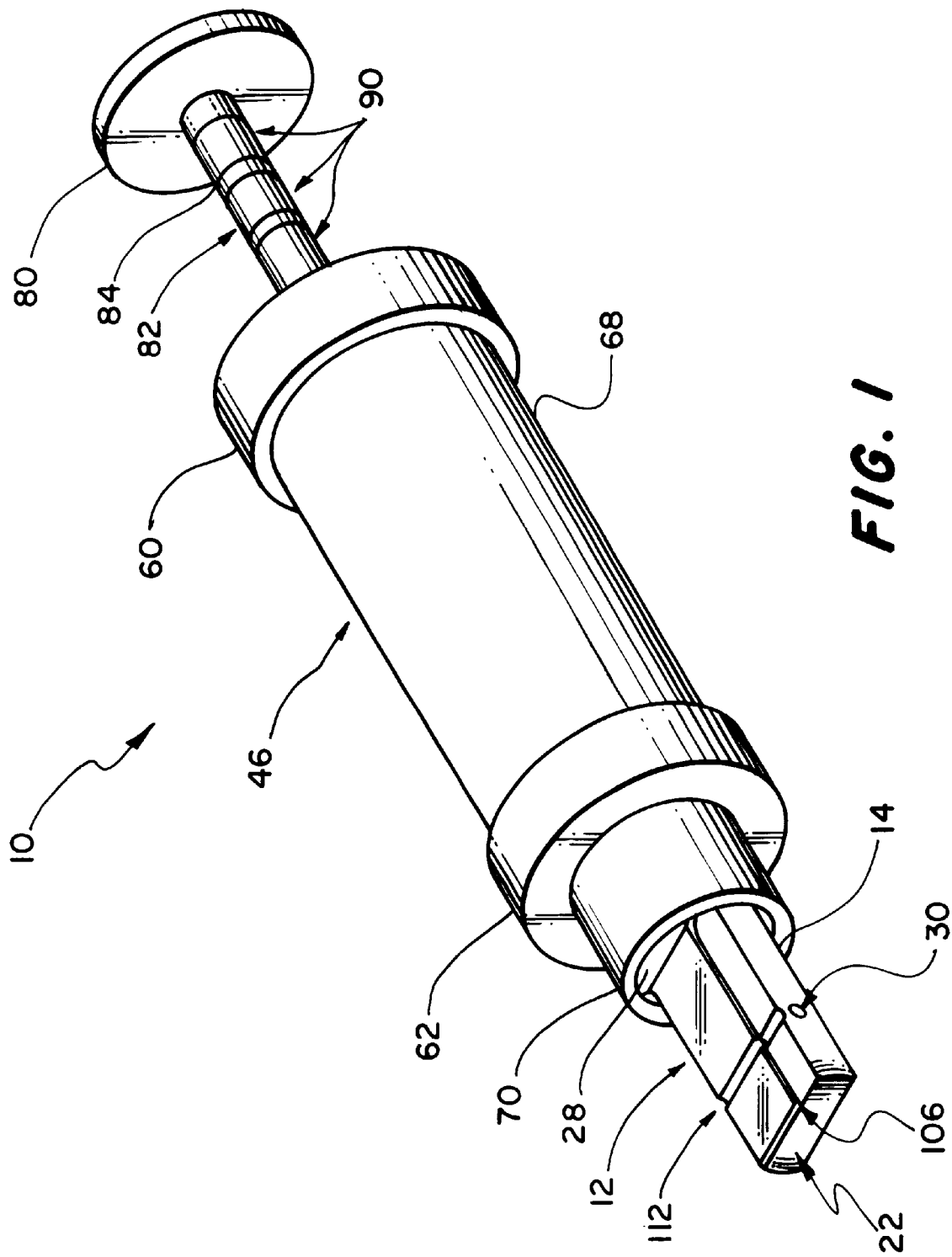
FIG. 1 is a perspective view of a seed-holding device, including a holder and a transfer device.

FIG. 1 is a perspective view of seed-holding system 10. System 10 includes holder 12 and transfer device 46. In FIG. 1, holder 12 and transfer device 46 are shown coupled.

Figure 7:
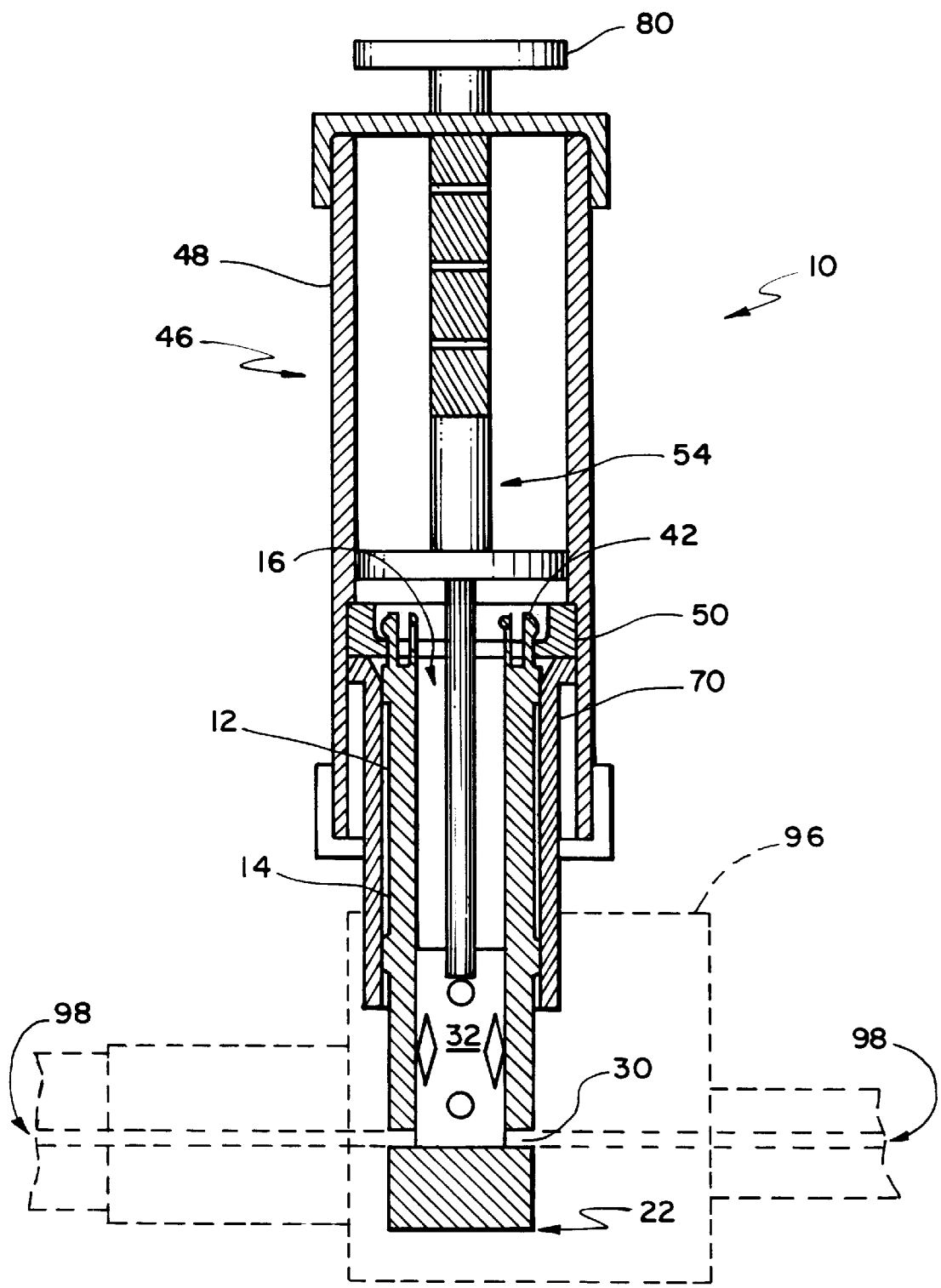
FIG. 7 is a cross-sectional view of a seed-holding device mated to an applicator.

Holder 12 stores one or more radioactive seeds. When seed-holding system 10 is mated to applicator 96 as shown in FIG. 7 and as described in more detail below, radioactive seeds may be dispensed from holder 12 one at a time though distal end bore 30. After a seed is dispensed, a new seed is forced into a position in which the new seed can be dispensed though distal end bore 30. The force used to move the new seed into position is supplied by expansive spring 94 (see FIG. 2) in transfer device 46.

In one embodiment, holder 12 is constructed of plastic, such as thermoplastic, and may be formed by several processes, such as molding. Thermoplastic construction offers many advantages, including inexpensive manufacture, disposability, and ease of sterilization. Plastic offers a further advance of allowing holder 12 to deform when coupling to and uncoupling from transfer device 46, as will be described more fully below. In addition, the plastic may be color-coded to identify the types of seeds contained within. For example, one color may indicate seeds including iodine-125, and another color may indicate seeds made of palladium-103.

Transfer device 46, in one embodiment, is constructed of metal such as stainless steel, and is reusable. When transfer device 46 is coupled to holder 12 as shown in FIG. 1, seed-holding system 10 can be mated to applicator 96, and radioactive seeds may be dispensed from holder 12. As a holder 12 is emptied of seeds, seed-holding system 10 may be disconnected from applicator 96, and empty holder 12 may be ejected from transfer device 46 and discarded. A fresh, full holder 12 may then be coupled to transfer device 46, and seed-holding system 10 may once again be mated to applicator 96.

Figure 2:
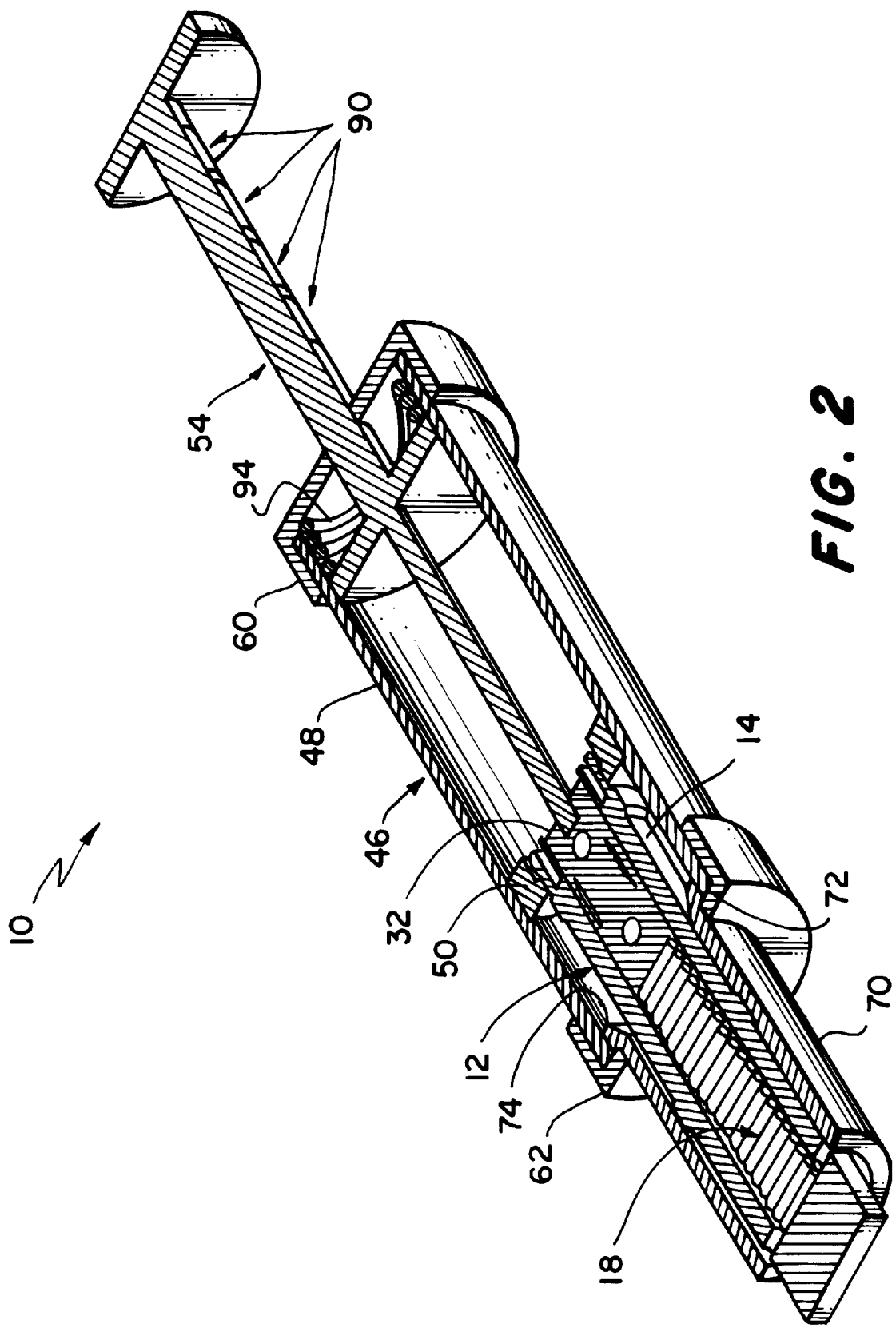
FIG. 2 is a cutaway view of a radioactive seed holding device, including a holder and a transfer device.
Figure 3:
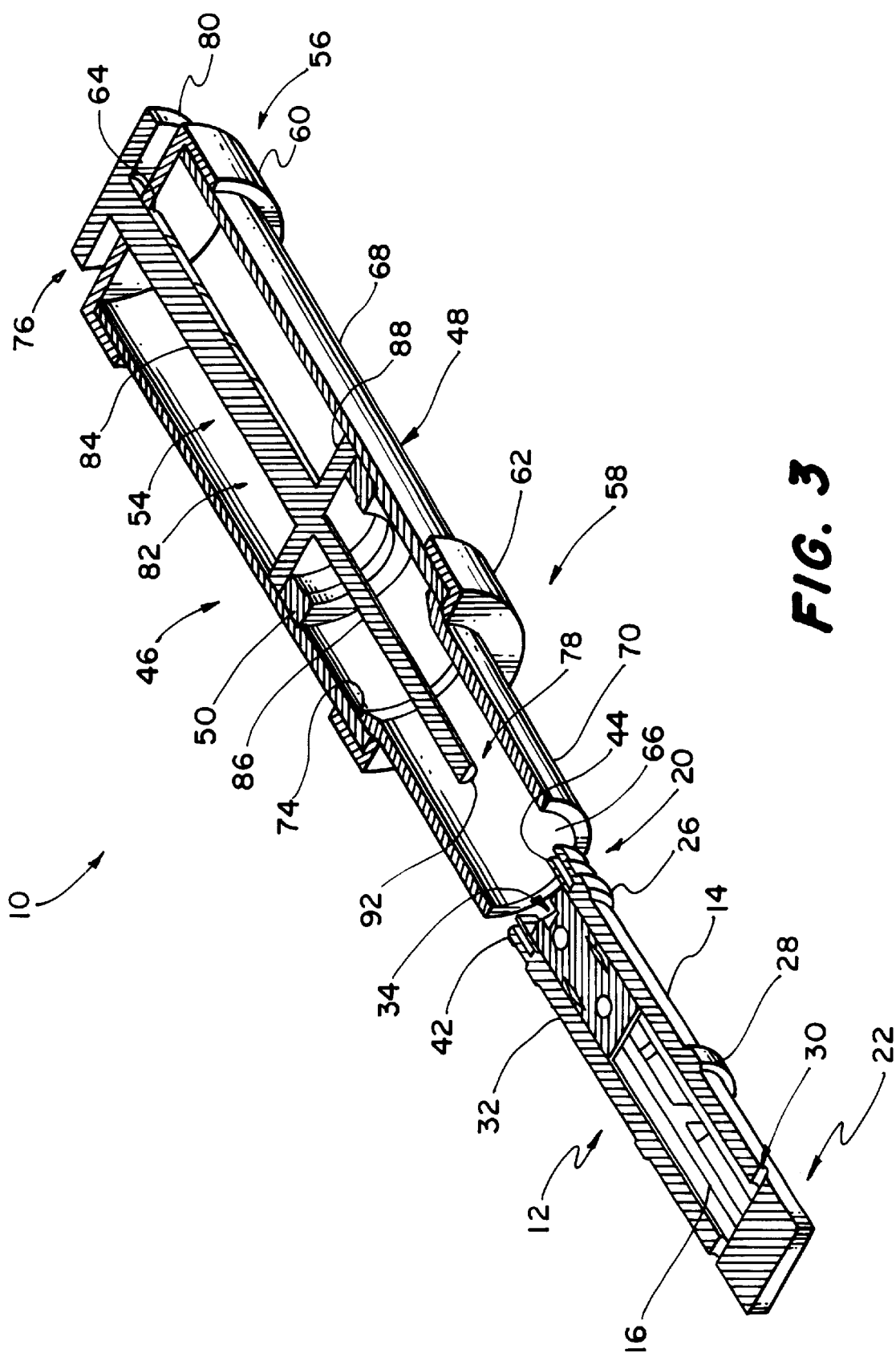
FIG. 3 is a cutaway view of a transfer device and a holder.

FIGS. 2 and 3 are cutaway views showing more details of holder 12 and transfer device 46. In FIG. 2, holder 12 and transfer device 46 are shown coupled, and in FIG. 3, holder 12 and transfer device 46 are shown separated.

Holder 12 includes main body 14 and pusher 32, shown cut away in FIGS. 2 and 3. Main body 14 defines a sleeve-like cavity 16, which holds a plurality of radioactive seeds 18. Main body 14 and/or pusher 32 can be color-coded. In addition, main body 14 can be made from a material (e.g., clear plastic) that allows the contents of holder 12 to be viewed. Each radioactive seed 18 is substantially cylindrical. In the embodiment depicted in FIG. 2, sleeve-like cavity 16 holds twenty radioactive seeds 18. (In FIG. 3, seeds 18 have been removed to show sleeve-like cavity 16 more clearly.) Seeds 18 are generally loaded into holder 12 by sliding seeds 18 laterally into sleeve-like cavity 16 at proximal end 20 of holder 12. Once seeds 18 are loaded into sleeve-like cavity 16, pusher 32 may be inserted into sleeve-like cavity 16 at proximal end 20 of holder 12, where pusher 32 abuts seeds 18. Techniques for loading seeds and inserting pusher 32 into sleeve-like cavity 16 will be described in more detail below. Seeds may be dispensed end-first from the distal end 22 of holder 12 through distal end bore 30.

Figure 4A:
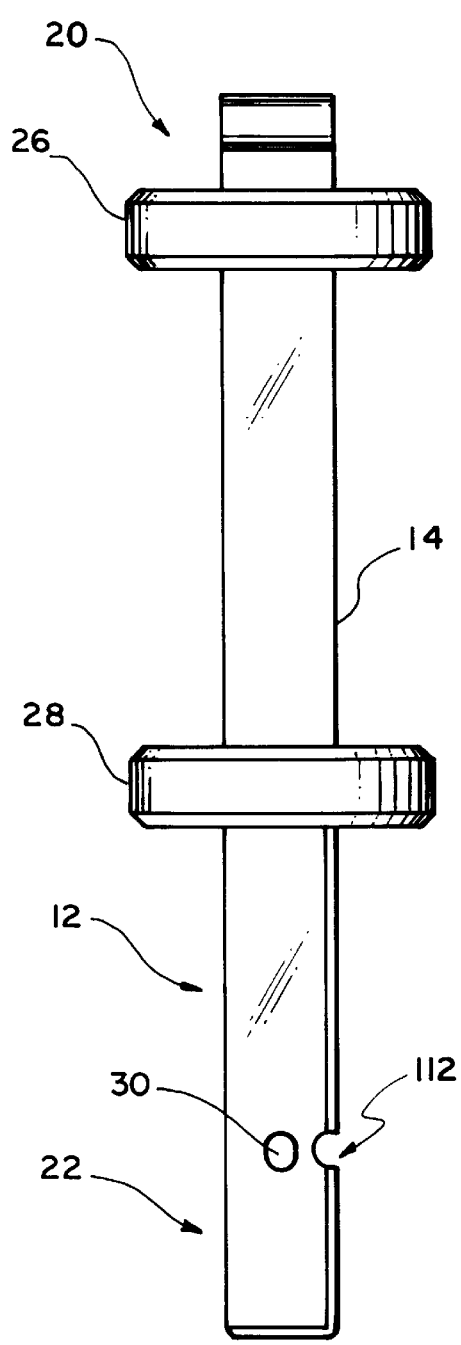
FIG. 4A is a left side view of a main body of a holder.
Figure 4B:
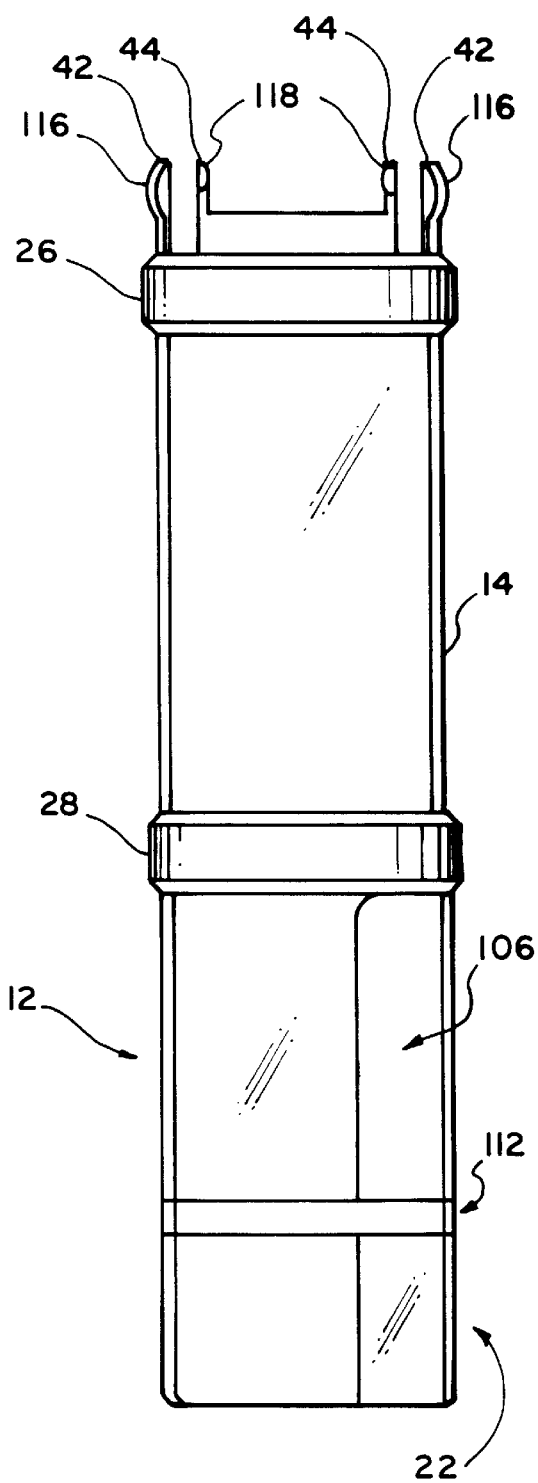
FIG. 4B is a front view of a main body of a holder.

Main body 14 of holder 12 is shown in more detail in FIGS. 4A and 4B. As shown in FIGS. 1, 2, 3, 4A and 4B, main body 14 is substantially planar, but main body 14 may assume a configuration other than planar. The shape of main body 14 ordinarily may be selected to allow holder 12 to fit into a slot of seed applicator 96. As shown in FIGS. 3, 4A and 4B, main body 14 of holder 12 includes optional proximal disk protrusion 26 and optional central disk protrusion 28. Disk protrusions 26 and 28 allow holder 12 to couple to transfer device 46, which is substantially cylindrical, and to prevent holder 12 from wobbling when coupled to transfer device 46. Main body 14 may include optional directional feature 106, as depicted in FIGS. 1 and 4B. Directional feature 106 is useful for keying holder 12 to a particular applicator, permitting coupling of holder 12 to the applicator in only one direction. In addition, holder 12 may optionally include securing feature 112, depicted in FIGS. 1, 4A and 4B as a groove. When seed-holding system 10 is inserted in a particular applicator, the applicator may be securely coupled to holder 12 by gripping securing feature 112. Directional feature 106 and securing feature 112 typically depend upon the applicator to which holder 12 will mate and upon the securing mechanism used by the applicator. Consequently, holders may be created with different conformations, each conformation configured to work with a different kind of applicator. Directional feature 106 and securing feature 112 shown in FIGS. 1, 4A and 4B are merely exemplary, and the invention is not limited to the features depicted.

Figure 5:
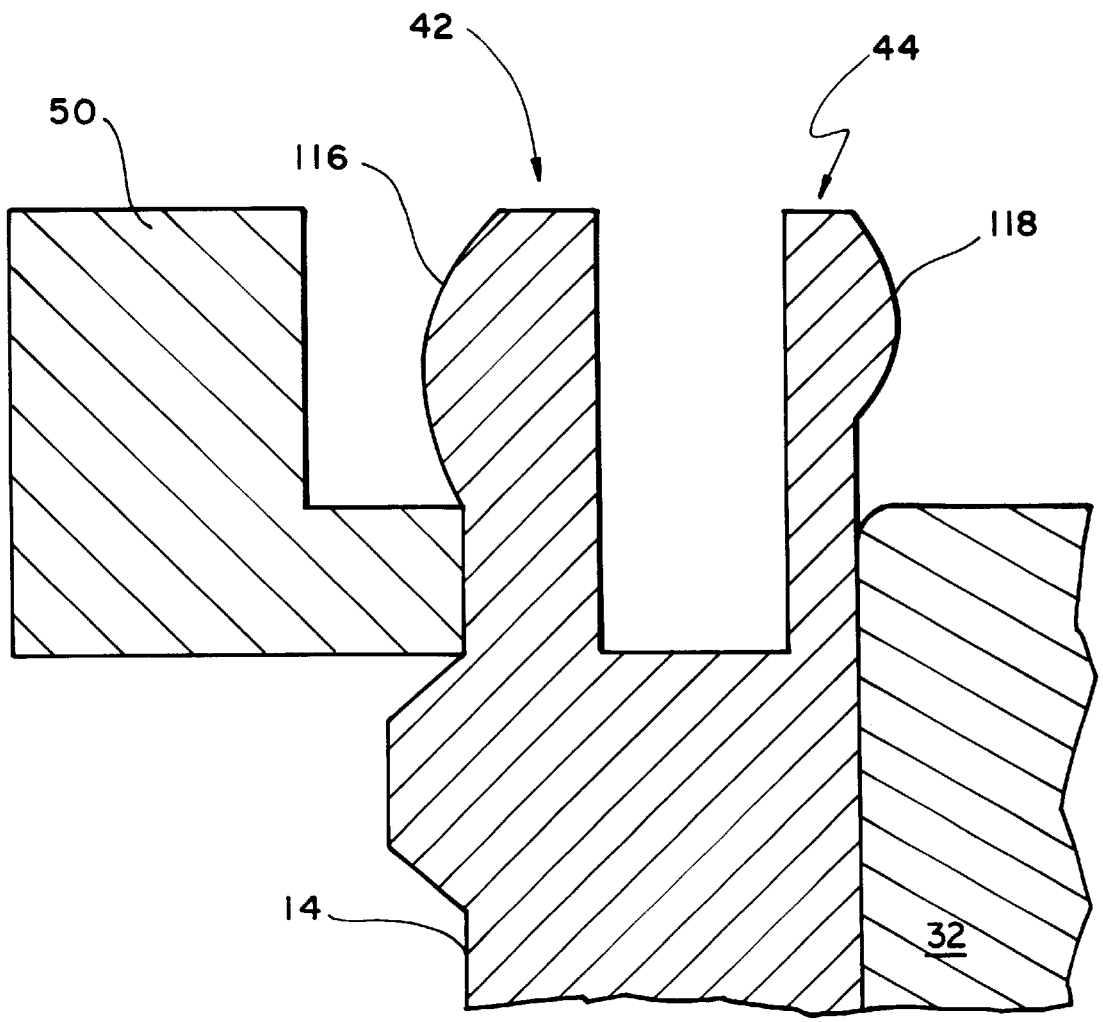
FIG. 5 is a cross-sectional view of finger-like projections of a holder engaged to a clamp ring of a transfer device.

As shown in FIGS. 3 and 4B, and as shown in more detail in FIG. 5, proximal end 20 of main body 14 includes two pairs of fingerlike structures, 42 and 44. As shown in the cross-sectional views of FIGS. 2 and 5, holder 12 couples to transfer device 46 by engaging fingerlike structures 42 with clamp ring 50. Outer pair of fingerlike structures 42 are configured to deform to slide over clamp ring 50 and snap into place. Outer pair of fingerlike structures 42 are further configured to deform upon application of distally directed pressure, as will be described in more detail below, thereby disengaging from clamp ring 50 and uncoupling holder 12 from transfer device 46.

Inner pair of fingerlike structures 44 provide added protection against accidental slippage of pusher 32 from sleeve-like cavity 16. If holder is accidentally dropped, for example, inner pair of fingerlike structures 44 reduce the risk that pusher 32 will be separated from main body 14, and thus reduce the risk of seed spillage.

Holder 12 can be loaded with seeds by a manufacturer or by a local medical staff member. Seeds can be obtained from any source such as a company specializing in brachytherapy. Typically, such companies provide seeds in bulk. To load holder 12, a person can count the seeds, verify the seeds' radioactivity, and place the seeds into sleeve-like cavity 16 of main body 14. Once loaded, holder 12 can be sterilized by, for example, autoclaving. Pusher 32 is useful in loading as well as in actual use of device 10.

Figure 6C:
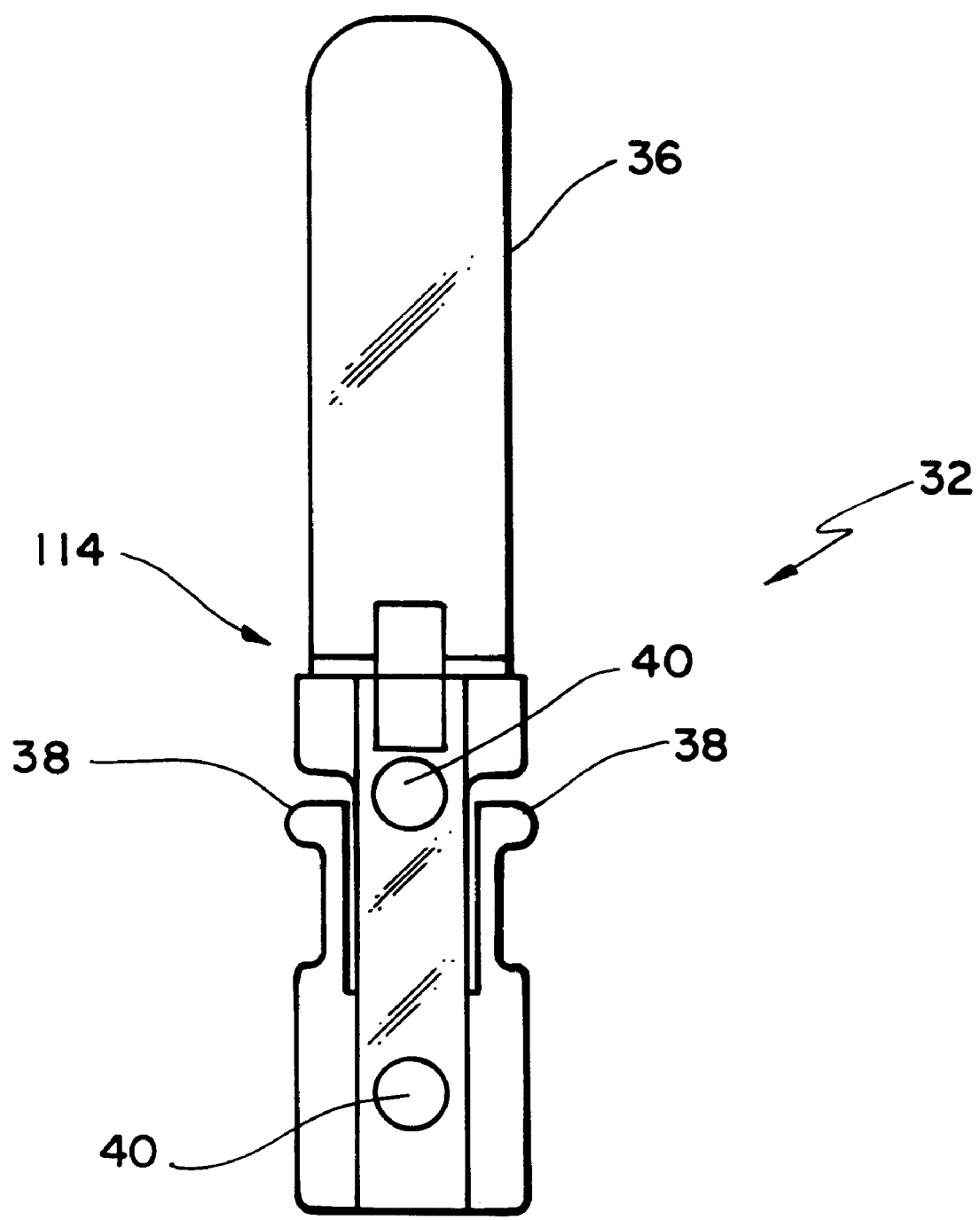
FIG. 6C is a front view of another embodiment of a pusher, with a handle.

FIG. 6A shows an embodiment of pusher 32. Pusher 32 includes notch 34 that receives distal end 92 of shaft 82 (shown in FIG. 3) of transfer device 46. Pusher 32 further includes drag structures 38, which allow pusher 32 to slide inside sleeve-like cavity 16 but which also prevent pusher 32 from sliding freely. As shown in FIG. 6A, drag structures 38 are in the form of side protrusions, with diamond-shaped apertures providing spring-like flexibility. Another embodiment of drag structures 38 is shown in FIG. 6C, in which drag structures 38 are cantilevered springs. FIGS. 6B and 6C show an optional temporary handle 36, useful in placing pusher 32 into sleeve-like cavity 16. When staff load main body 14 with seeds, pusher 32 can be used as a tamp to assure the seeds are properly seated in sleeve-like cavity 16. Temporary handle 36 allows pusher to be easily inserted into sleeve-like cavity 16 and to be easily withdrawn. Temporary handle 36 is coupled to pusher 32 by snap-off connection 114. Once main body 14 is loaded and pusher 32 is inserted into sleeve-like cavity 16 and placed in contact with stack of seeds 18, temporary handle 36 can be snapped off and discarded. If it is later necessary to remove pusher 32 from sleeve-like cavity 16, a tool may be used to grab removal features 40 of pusher 32 and extract pusher 32. Removal features 40 may be structures such as protrusions, indentations or apertures. Drag structures 38, temporary handle 36 and removal features 40 may be integrally formed with pusher 32 during the formation process.

Transfer device 46 can contain metal (e.g., stainless steel) to provide radiation shielding. It will be understood that transfer device 46 can be made of other materials as well (e.g., molded plastic). In addition to providing radiation shielding, metal construction provides advantages such as increased durability and ease of sterilization. As shown in FIGS. 1, 2 and 3, transfer device 46 includes housing 48. Housing 48 need not be substantially cylindrical as shown in FIGS. 1, 2 and 3, but cylindrical configuration allows housing to flexibly couple to different conformations of holders 12. When housing 48 is substantially cylindrical, transfer device 46 can have an outer shape that prevents the transfer device 46 from rolling across a flat surface (e.g., a table). For example, transfer device 46 can have a flat boss (not shown) to prevent rolling.

Because housing 48 is the component of transfer device 46 that is most likely to be touched and handled, exterior surface 68 of housing 48 may be coated or textured to make housing 48 easier to grasp. In the embodiment depicted in FIGS. 1, 2 and 3, housing 48 is a cylindrically shaped casing coupled to proximal end cap 60 and distal end cap 62. These components may be produced in many ways, such as from rod and tubing stock by machining, and may be joined in several ways, such as by threads, interference press fit or adhesive bonding. Housing 48 may be formed in other ways, such as by joining complementary molded halves. Housing 48 encases clamp ring 50, which is held in a fixed position relative to housing 48. Clamp ring 50 may be a separate component joined to housing 48, or may be formed integrally with housing 48. In one embodiment, housing 48, proximal end cap 60, distal end cap 62, and clamp ring 50 are formed integrally as two identical halves that can be joined together. For example, housing 48, proximal end cap 60, distal end cap 62, and clamp ring 50 can be made of two identical molded plastic pieces that are joined together to form a single unit.

When housing 48 is made of plastic, a first metal inner lining (not shown) can be fitted inside housing 48. The first inner lining can be fitted inside housing 48 such that the first metal inner lining extends from proximal end cap 60 to clamp ring 50. Likewise, a second metal inner lining (not shown) can be fitted inside housing 48 such that, for example, the second metal inner lining extends from clamp ring 50 to distal end cap 62. Typically, the first and second metal inner linings have a shape corresponding to the inner shape defined by housing 48. For example, if housing 48 defines an inner shape that is cylindrical, then the first and second metal inner linings can be cylindrical. Typically, the first and second metal inner linings are designed to provide radiation shielding. Any method can be used to make transfer device 46 fitted with first and second metal inner linings within housing 46. For example, the first and second metal inner linings can be hollow metal tubes. Such hollow metal tubes can be fitted within two identical halves of molded plastic that can be joined together. Once joined together, the two identical halves of molded plastic can define housing 48, proximal end cap 60, distal end cap 62, and clamp ring 50.

When housing 48 is made of plastic, a metal outer lining (not shown) can be fitted outside housing 48. The metal outer lining can be fitted outside housing 48 such that the metal outer lining extends from proximal end cap 60 to distal end cap 62. Typically, the metal outer linings have a shape corresponding to the outer shape defined by housing 48. For example, if housing 48 defines an outer shape that is cylindrical, then the metal outer lining can be cylindrical. Typically, the metal outer lining is designed to provide radiation shielding. In one embodiment, housing 48 can be fitted with a metal inner lining and a metal outer lining. For example, housing 48 can be fitted with a metal inner lining that extends from proximal end cap 60 to clamp ring 50 and a metal outer lining that extends from clamp ring 50 to distal end cap 62.

Distal end cap 62 defines distal end opening 66, through which shield 70 extends and retracts. Shield 70 is substantially cylindrical, with an outer diameter slightly smaller than the inner diameter of housing 48, allowing shield 70 to extend and withdraw. Flange 74 on shield 70 prevents shield 70 from slipping through distal end opening 66. Although shield 70 may be spring-loaded or otherwise biased to assume an extended position, shield 70 may also deploy by gravity. Shield 70 is shown in FIG. 1 in a partially retracted position, and is shown in FIGS. 2 and 3 in a fully extended position. When extended, shield 70 covers holder 12 and the seeds 18 within holder 12, thus providing enhanced radiation shielding.

Proximal end 56 of housing 48 is enclosed, except for opening 64 in proximal end cap 60, through which shaft 82 of pusher assembly 54 slides. As shown in FIGS. 2 and 3, pusher assembly 54 includes push disk 80, which is external to housing 48. As will be described below, push disk 80 is used to eject holder 12 from transfer device 46. Push disk 80 is affixed to shaft 82. Shaft 82 includes upper portion 84 and lower portion 86. Upper portion 84 extends from push disk 80 through proximal end opening 64 to spring plate 88. Lower portion 86 of shaft 82 extends from spring plate 88 toward distal end 58 of transfer device 46. Push disk 80, upper portion 84 and lower portion 86 of shaft 82 and spring plate 88 may be formed from separate components and joined together, or may be formed as an integral unit. In addition, push disk 80, upper portion 84 and lower portion 86 of shaft 82 and spring plate 88 can be made of any material (e.g., metal or plastic). A metal construction can provide radiation shielding. For example, when housing 48, proximal end cap 60, distal end cap 62, and clamp ring 50 are formed integrally as molded plastic, first and second metal inner linings and a spring plate 88 made of metal can be used to provide radiation shielding.

When fully-loaded holder 12 is inserted into transfer device 46, distal end 92 of shaft 58 engages notch 34 of pusher 32. As holder 12 is inserted farther into transfer device 46, expansive spring 94 is compressed and upper portion 84 of shaft 82 is pushed further outside of housing 48. When fingerlike structures 42 engage clamp ring 50, upper portion 84 of shaft 82 is fully extended outside housing 48. As seeds are dispensed from seed-holding system 10, upper portion 84 descends incrementally into housing 48. When all seeds are dispensed, most of upper portion 84 is inside housing 48. Consequently, the percentage of upper portion 84 that is outside housing 48 at any particular time, and therefore visible to the user of device 10, is a function of the number of seeds in holder 12. Graduated marks 90 placed on upper portion 84 of shaft 82 may be used to provide visual feedback of the number of seeds remaining in holder 12. Graduated marks 90 may be, for example, etched into the metal or painted on upper portion 84.

Transfer device 46 provides spring-loading for seeds 18 in holder 12. Expansive spring 94 (shown in FIG. 2 but omitted from other figures for clarity) is located between spring plate 88 and proximal end cap 60. Spring 94 drives spring plate 88 away from proximal end 56 of housing 48. When a fully-loaded holder 12 is inserted into transfer device 46 and fingerlike structures 42 engage clamp ring 50, spring 94 is placed in compression as shown in FIG. 2. As spring 94 exerts force against spring plate 88, lower portion 86 of shaft 82, which is coupled to spring plate 88, exerts force against pusher 32. Pusher 32 in turn exerts force against seeds 18. As a seed is dispensed through distal end bore 30, spring 94 causes shaft 82 to move incrementally into toward distal end 58 of housing 48, causing pusher 32 to push remaining seeds 18 distally, thereby aligning a new seed with distal end bore 30.

FIG. 7 shows seed-holding system 10 mated to an exemplary applicator 96. Applicator 96 may be one of many instruments used in brachytherapy procedures, such as a Mick applicator. The opening in applicator 96 that receives device 10 causes shield 70 to retract while allowing distal end bore 30 of holder 12 to align with applicator bore 98. In a typical applicator, a push rod (not shown) slides back and forth through applicator bore 98 to push seeds through applicator bore 98 into an implantation needle (not shown). When seed-holding system 10 is mated to applicator 96, the push rod can slide through distal end bore 30, thereby pushing a seed end-first out of holder 12 and into applicator bore 98. After the seed is dispensed and the push rod withdrawn, spring 94 drives shaft 82 and pusher 32 distally, bringing a new seed in position in distal end bore 30, ready to be dispensed.

As shown in FIG. 7, seed-holding system 10 is empty. In this state, a push rod is prevented from extending through holder 12 because the push rod's path through distal end bore 30 is obstructed by pusher 32. The seed holding system 10 is ready to be disengaged from applicator 96. Once seed-holding system 10 is disengaged from applicator 96, empty holder 12 is ejected by holding housing 48 of transfer device 46, and pushing on push disk 80. Pushing on push disk 80 drives pusher assembly 54 distally, which drives pusher 32 against distal end bore 30. Pusher 32 is at the end of sleeve-like cavity 16 and cannot advance further. As a result, pressure on push disk 80 overcomes the engagement of outer fingerlike structures 42 with clamp ring 50. Outer fingerlike structures 42 deform and disengage from clamp ring 50, allowing holder 12 to be easily removed from transfer device 46.

A number of embodiments of the present invention have been described. Nevertheless, various modifications may be made without departing from the spirit and scope of the inventions as set forth in the claims that follow. For example, seed-holding system 10 may hold spacers in addition to radioactive seeds. Spacers are non-radioactive objects usually similar in size to radioactive seeds. Spacers interspersed between radioactive seeds are useful in placing radioactive seeds at desired depths within tissue.

What is claimed is:

1. A device comprising:
   (a) a holder configured to receive at least one radioactive seed, comprising a main body and a pusher that slides in the main body; and
   (b) a transfer device configured to engage the holder, the transfer device defining a proximal end and a distal end and comprising a housing, an expansive spring and a pusher assembly, the pusher assembly configured to engage the pusher, and the expansive spring configured to drive the pusher assembly toward the distal end of the transfer device;
   wherein the transfer device further comprises a clamp ring coupled to the housing, and wherein the holder further comprises at least one fingerlike structure coupled to the main body, the fingerlike structure configured to engage the clamp ring.

2. The device of claim 1, wherein the holder is configured to couple to a seed applicator.

3. The device of claim 1, wherein the main body defines a proximal end and a distal end, and wherein the proximal end of the main body is configured to receive the radioactive seed.

4. The device of claim 1, wherein the main body defines a proximal end and a distal end, and wherein the distal end of the main body is configured to dispense the seed.

5. The device of claim 1, wherein the transfer device comprises a shield configured to extend from the distal end of the transfer device.

6. The device of claim 5, wherein the shield, when extended, encompasses at least a portion of the holder.

7. The device of claim 1, wherein the main body and pusher are made of thermoplastic.

8. The device of claim 1, wherein at least a portion of the main body is color-coded.

9. The device of claim 1, wherein the contents of the holder are viewable through the material of at least a portion of the main body.

10. The device of claim 1, wherein the transfer device comprises metal.

11. The device of claim 10, wherein the transfer device is made of stainless steel.

12. The device of claim 1, wherein the transfer device comprises metal and plastic.

13. The device of claim 1, wherein the pusher assembly comprises a push disk and a spring plate coupled to a shaft.

14. The device of claim 1, wherein the distal end defines a distal end bore, and wherein the pusher obstructs the distal end bore in the absence of radioactive seeds.

15. The device of claim 1, wherein at least a portion of the holder is encompassed by a shield that movably extends from and retracts into the distal end of the transfer device.

16. The device of claim 15, wherein the shield is movable by spring force.

17. The device of claim 15, wherein the shield is movable by gravity force.

18. A device comprising:
   (a) a holder configured to receive at least one radioactive seed, comprising a main body and a pusher that slides in the main body; and
   (b) a transfer device configured to engage the holder, the transfer device defining a proximal end and a distal end and comprising a housing, an expansive spring and a pusher assembly, the pusher assembly configured to engage the pusher, and the expansive spring configured to drive the pusher assembly toward the distal end of the transfer device,
   wherein the pusher assembly comprises a push disk and a spring plate coupled to a shaft.

19. The device of claim 18, wherein the holder is configured to couple to a seed applicator.

20. The device of claim 18, wherein the main body defines a proximal end and a distal end, and wherein the proximal end of the main body is configured to receive the radioactive seed.

21. The device of claim 18, wherein the main body defines a proximal end and a distal end, and wherein the distal end of the main body is configured to dispense the seed.

22. The device of claim 18, wherein the transfer device comprises a shield configured to extend from the distal end of the transfer device.

23. The device of claim 22, wherein the shield, when extended, encompasses at least a portion of the holder.

24. The device of claim 18, wherein the main body and pusher are made of thermoplastic.

25. The device of claim 18, wherein at least a portion of the main body is color-coded.

26. The device of claim 18, wherein the contents of the holder are viewable through the material of at least a portion of the main body.

27. The device of claim 18, wherein the transfer device comprises metal.

28. The device of claim 27, wherein the transfer device is made of stainless steel.

29. The device of claim 18, wherein the transfer device comprises metal and plastic.

30. The device of claim 18, wherein the transfer device further comprises a clamp ring coupled to the housing and the holder further comprises at least one fingerlike structure coupled to the main body, the fingerlike structure configured to engage the clamp ring.

31. The device of claim 18, wherein the distal end defines a distal end bore, and wherein the pusher obstructs the distal end bore in the absence of radioactive seeds.

32. The device of claim 18, wherein at least a portion of the holder is encompassed by a shield that movably extends from and retracts into the distal end of the transfer device.

33. The device of claim 32, wherein the shield is movable by spring force.

34. The device of claim 32, wherein the shield is movable by gravity force.

35. A device comprising:
(a) a holder configured to receive at least one radioactive seed, comprising a main body and a pusher that slides in the main body; and
(b) a transfer device configured to engage the holder, the transfer device defining a proximal end and a distal end and comprising a housing, an expansive spring and a pusher assembly, the pusher assembly configured to engage the pusher, and the expansive spring configured to drive the pusher assembly toward the distal end of the transfer device;
wherein at least a portion of the holder is encompassed by a shield that movably extends from and retracts into the distal end of the transfer device.

36. The device of claim 35, wherein the shield is movable by spring force.

37. The device of claim 35, wherein the shield is movable by gravity force.

38. The device of claim 35, wherein the holder is configured to couple to a seed applicator.

39. The device of claim 35, wherein the main body defines a proximal end and a distal end, and wherein the proximal end of the main body is configured to receive the radioactive seed.

40. The device of claim 35, wherein the main body defines a proximal end and a distal end, and wherein the distal end of the main body is configured to dispense the seed.

41. The device of claim 35, wherein the main body and pusher are made of thermoplastic.

42. The device of claim 35, wherein at least a portion of the main body is color-coded.

43. The device of claim 35, wherein the contents of the holder are viewable through the material of at least a portion of the main body.

44. The device of claim 35, wherein the transfer device comprises metal.

45. The device of claim 44, wherein the transfer device is made of stainless steel.

46. The device of claim 35, wherein the transfer device comprises metal and plastic.

47. The device of claim 35, wherein the transfer device further comprises a clamp ring coupled to the housing and the holder further comprises at least one fingerlike structure coupled to the main body, the fingerlike structure configured to engage the clamp ring.

48. The device of claim 35, wherein the pusher assembly comprises a push disk and a spring plate coupled to a shaft.

49. The device of claim 35, wherein the distal end defines a distal end bore, and wherein the pusher obstructs the distal end bore in the absence of radioactive seeds.

* * * * *

UNITED STATES PATENT AND TRADEMARK OFFICE
CERTIFICATE OF CORRECTION

PATENT NO.    : 6,572,527 B2
DATED         : June 3, 2003
INVENTOR(S)   : Martin T. Steele, Sr. et al.

It is certified that error appears in the above-identified patent and that said Letters Patent is hereby corrected as shown below:

<u>Title page,</u>
Item [75], Inventor, please add -- Charles R. Pitman --

Signed and Sealed this

Sixteenth Day of December, 2003

JAMES E. ROGAN
*Director of the United States Patent and Trademark Office*